(12) United States Patent
Dose et al.

(10) Patent No.: US 10,197,561 B2
(45) Date of Patent: Feb. 5, 2019

(54) CELL DETECTION WITH CONJUGATES HAVING AN ENZYMATICALLY RELEASABLE DETECTION MOIETY

(71) Applicant: Miltenyi Biotec GmbH, Bergisch Gladbach (DE)

(72) Inventors: Christian Dose, Kurten (DE); Jennifer Brieden, Ennepetal (DE); Stefan Miltenyi, Bergisch Gladbach (DE); Thomas Rockel, Düsseldorf (DE); Veronika Gann, Bergisch Gladbach (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 274 days.

(21) Appl. No.: 14/944,352

(22) Filed: Nov. 18, 2015

(65) Prior Publication Data
US 2016/0187326 A1 Jun. 30, 2016

(30) Foreign Application Priority Data

Dec. 27, 2014 (EP) ..................... 14200361

(51) Int. Cl.
*G01N 33/542* (2006.01)
*G01N 33/569* (2006.01)
*G01N 33/53* (2006.01)
*G01N 33/537* (2006.01)

(52) U.S. Cl.
CPC ....... *G01N 33/542* (2013.01); *G01N 33/5306* (2013.01); *G01N 33/537* (2013.01); *G01N 33/56972* (2013.01)

(58) Field of Classification Search
CPC ............. G01N 33/5306; G01N 33/537; G01N 33/542; G01N 33/56972
See application file for complete search history.

(56) References Cited

U.S. PATENT DOCUMENTS

2014/0295458 A1* 10/2014 Schmidt ............... G01N 33/557
435/7.21

FOREIGN PATENT DOCUMENTS

| DE | 10143757 | 3/2003 |
| EP | 2 725 358 | 4/2014 |
| GB | 2372356 | 8/2002 |
| WO | WO 96/31776 | 10/1996 |
| WO | WO 02/054065 | 7/2002 |
| WO | WO 2013/011011 | 1/2013 |

OTHER PUBLICATIONS

A machine translation of DE 10143757.*

* cited by examiner

*Primary Examiner* — Galina Yakovleva
(74) *Attorney, Agent, or Firm* — Jaquelin K. Spong (57) ABSTRACT

The invention is directed to a method for detecting a target moiety in a sample of biological specimens by:
a) providing at least one conjugate with the general formula (I) $X_n$—P—$Y_m$, with X is an detection moiety, P an enzymatically degradable spacer and Y an antigen recognizing moiety and n, m are integers between 1 and 100 and wherein X and Y are covalently bound to P;
b) contacting the sample of biological specimens with at least one conjugate, thereby labeling the target moiety recognized by the antigen recognizing moiety Y;
c) detecting the target moiety labeled with the conjugate with the detecting moiety X; and
d) enzymatically degrading spacer P, thereby cleaving the detection moiety X from the conjugate.
The method is useful to identify target moieties on the biological specimens. The biological specimens detected by the conjugate can be subsequently removed from the sample.

2 Claims, 7 Drawing Sheets

CELL DETECTION WITH CONJUGATES HAVING AN ENZYMATICALLY RELEASABLE DETECTION MOIETY

CROSS REFERENCE TO RELATED APPLICATIONS

Not applicable.

STATEMENT REGARDING FEDERALLY SPONSORED RESEARCH

Not applicable.

STATEMENT REGARDING MICROFICHE APPENDIX

Not applicable.

BACKGROUND

The present invention is directed to a process for detection or identification of target moieties or target cells or from a cell sample.

Fluorescent dyes conjugated to one or more antibodies are commonly used for immunofluorescence analysis. A vast number of variants in view of antibodies, fluorescent dyes, flow cytometers, flow sorters, and fluorescence microscopes has been developed in the last two decades to enable specific detection and isolation of target cells. One issue in immunofluorescence technology is the detection threshold of the fluorescence emission, which can be enhanced, for example, by better detectors, filter systems, lasers, or modified fluorescent dyes i.e. with better quantum yield.

Although fluorescent labelling has found widespread use, it is by no means the only way of labelling and detecting cells. Besides fluorescent dyes other detection moieties have found use, such as transition metal isotope mass tag labelling or radioactive isotope labelling. Detection of labels is then performed with mass cytometry or scintillation assays.

Isolating target cells with flow sorting using fluorochrome-conjugates targeting the antigen of interest results in highly purified target cell fractions. One disadvantage is that after the sorting process cells are still labeled with the fluorochrome-conjugate used for the detection and identification during the sorting process.

As described for the isolation of antigen-specific T-cells with MHC-Multimers, disposition of labeling may affect target cells (U.S. Pat. No. 7,776,562). To avoid alterations of the cells, a release of fluorescent moiety and antigen recognizing moiety is possible after detection and/or sorting. U.S. Pat. No. 7,776,562 discloses a method of reversible fluorescent labeling based on indirect, non-covalent labeling of target cells with reversible peptide/MHC-Multimers or Fab-Streptamers. Low-affinity peptide/MHC- or Fab-monomers with StreptagII are multimerized via streptactin to provide complexes with high avidity for the target antigen. Reversibility of multimerization and monomerization is initiated by addition of the competitor Biotin. After dissociation of low-affinity peptide/MHC- or Fab-monomers the antigen is released from the interaction partners. Beside StreptagII/Streptactin-interaction another indirect binding interaction is described for reversible magnetic cell separation based on a PEO-Biotin/anti-Biotin-antibody interaction (EP2725359 A1).

WO20080918100 discloses a conjugate wherein an enzyme acts as activator for a fluorescent dye, which can be released from the target cells by radiation induced cleaving of the enzyme.

Figure 1:
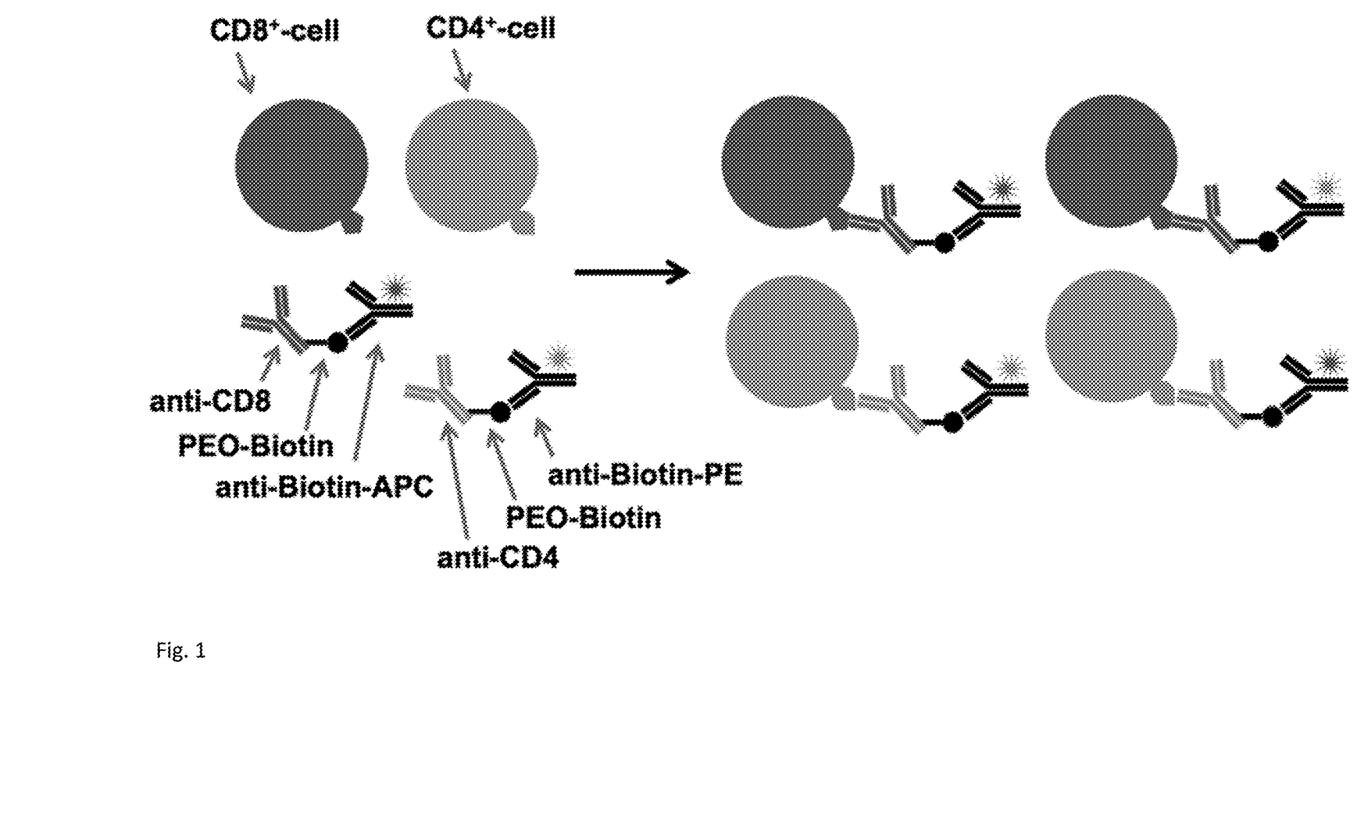
FIG. 1 shows reversible staining with the indirect labelling system based on Biotin/anti-Biotin interaction according to the prior art.
Figure 2:
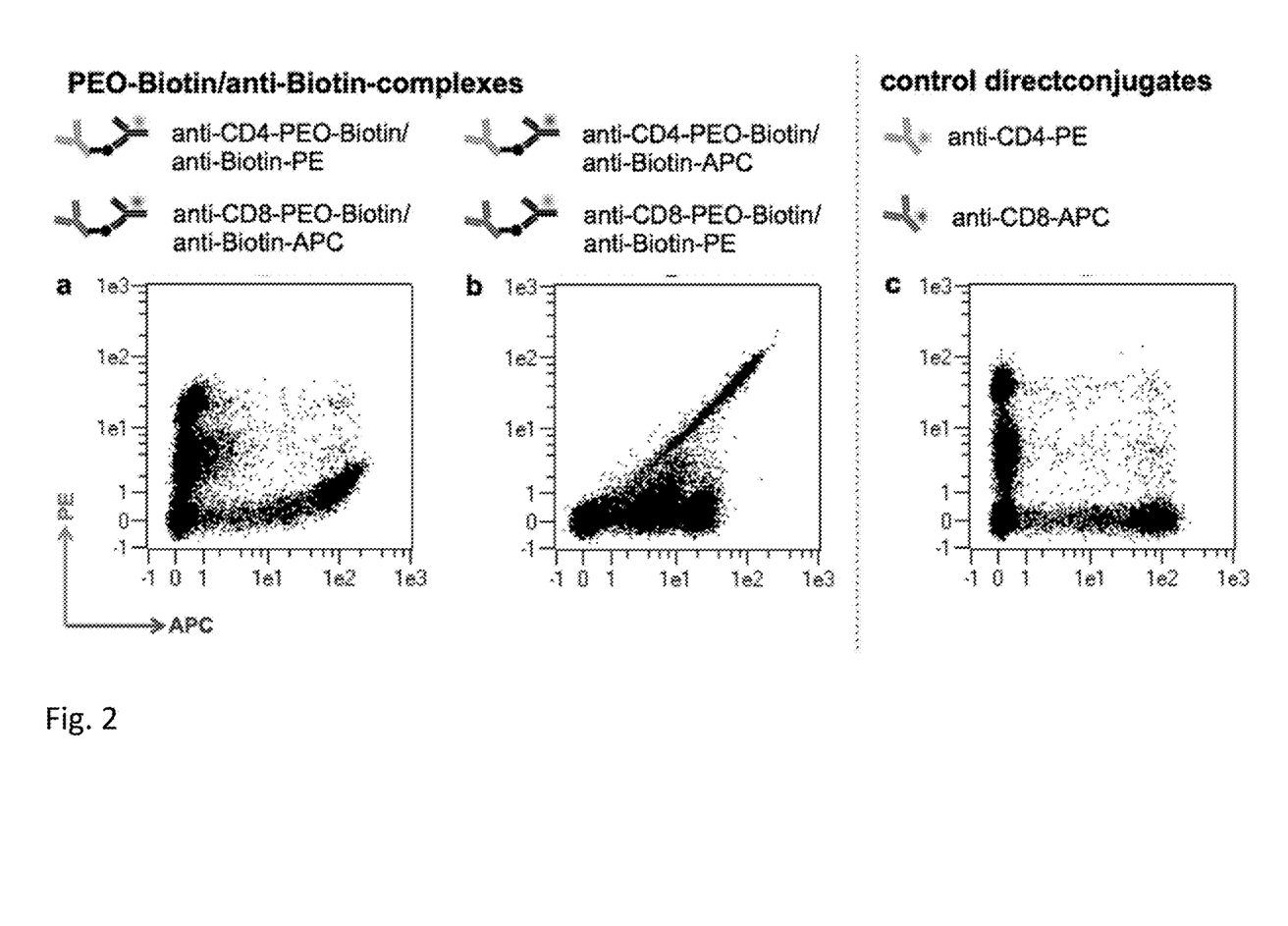
FIG. 2 shows simultaneous staining of cells with the indirect labelling system according to the prior art, based on Biotin/anti-Biotin interaction in equilibrium.

Multiple parameter labeling can be used to define and target more than one cell population or a specific subpopulation. However, depending on the respective equilibrium constant, a target cell labelled with a first antibody conjugate will be de-labelled after some time and re-labeled with either the first antibody conjugate again or with a second antibody conjugate. In the latter case, the information obtained will be a combination of the first and second labeling. Accordingly, simultaneous labelling with more than one antibody conjugate may reveal drawbacks as visualized in FIG. 1 and FIG. 2. FIG. 1 shows the mixture obtained by contacting two populations of cells (CD4 and CD8) with anti-CD8-PEO-Biotin/anti-Biotin-APC and anti-CD4-PEO-Biotin/anti-Biotin-PE. Due to the reversible nature of the Biotin/anti-Biotin complex, the resulting equilibrium comprises 4 instead of 2 cell-dye conjugates. The resulting equilibrium is determined by the kinetic and thermodynamic characteristic of the complexes and is reached after an exchange of the different binding partners leading to a fluorescent labeling of each target antigen with both fluorescent moieties. Instead of a specific labeling, a nearly unpredictable mixture is achieved. FIGS. 2a and b show two examples of this effect. The degree of exchange depends on parameters, like the selection of anti-Biotin-fluorochrome-conjugate as demonstrated in FIGS. 2a and b, as well as the concentration of the components of the complex. Therefore reversible fluorescent labeling based on reversible indirect systems is only suitable for single parameter and not for multiple parameter labeling. Compared to reversible indirect systems covalent conjugated antigen recognizing moiety and detection moiety provide specific labeling with the possibility to target multiple parameters. An example of a specific labeling of $CD4^+$- and $CD8^+$-target cells with covalently conjugated anti-CD4-PE and anti-CD8-APC is shown in FIG. 2c.

Besides reversible systems based on specific competition of indirect, non-covalent binding interactions between antigen recognizing moiety and detection moiety, for magnetic cell separation several other reversible systems were developed. Known methods to release magnetic particles from target cells after separation are mechanical agitation or chemically or enzymatically cleavable linker to the magnetic particles. For example, U.S. Pat. No. 6,190,870 and WO 96/31776 discloses magnetic cell separation based on magnetic particles coated with dextran and/or linked via dextran to the antigen recognizing moiety. Subsequent cleavage of the isolated target cells from the magnetic particle is initiated by the addition of the dextran-degrading enzyme dextranase. Besides dextran-based magnetic particles the digestion of dextran-fluorochrome-conjugates is described in U.S. Pat. No. 5,719,031. In this case, the degree of labeling of dextran-fluorochrome-conjugates is high enough to furnish fluorescent quenching. Therefore degradation is accompanied by an enhancement of fluorescence emission signal, which is used for the quantification of the enzymatic digestion process.

Fluorescence quenching by connecting fluorescent dyes is also described in GB2372256. Cells are stained with a conjugate comprising a plurality of fluorescent dyes attached via a linker to an antibody. Since the high density of fluorescent dyes will quench the fluorescence signals, GB2372256 describes an enzymatic degradation of the linker in order to release fluorescent dyes from the conjugate. The released fluorescent dyes are not subject to selfquenching, resulting in more intense fluorescence signals, i.e. in better resolution. However, since the fluorescence signals are detected after release from the target, the identification of target moieties on the cell surface is not possible with the method according to GB2372256. Furthermore, it is not possible to detect more than one target simultaneously, since the resulting mix of fluorescence signals cannot be assigned to a specific conjugate and/or target.

Elimination of the fluorescence signal is essential for immunofluorescence technologies based on sequentially staining specimens. These technologies have been shown to provide a higher multiplexing potential compared to standard procedures using simultaneously labeling and detection. However, these technologies are based on oxidative destruction of conjugated fluorescent moieties by photo- or chemical bleaching procedures (U.S. Pat. No. 7,741,045 B2, EP 0810 428 B1 or DE10143757) and are subjected to steric hindrances by antibodies remaining on the specimen.

Besides chemical bleaching procedures to eliminate the fluorescence signal, DE 10143757 proposes the elimination of the fluorescence signal by enzymatic degradation of the antibodies. The enzymatic degradation of antibodies depends highly on the structure of the antibody and requires a specific selection of a "matching" pair of enzyme and antibody.

SUMMARY

It was therefore an object of the invention to provide a method for specific labelling and detection of a target in or on a sample of a biological specimen and subsequently removing the detection moiety in order to provide reversible labelling and/or enable further different labelling and detection cycles.

Surprisingly it was found that conjugates composed of an antigen binding moiety linked via an enzymatically degradable spacer to a detection moiety can be enzymatically degraded thereby releasing the detection moiety from the biological specimen. After release, the biological specimen can be subjected to the same or a different conjugate again without interference of the previous label.

Object of the invention is therefore a method for detecting a target moiety in a sample of biological specimens by:
a) Providing at least one conjugate with the general formula (I) $X_n$—P—$Y_m$, with X is an detection moiety, P an enzymatically degradable spacer and Y an antigen recognizing moiety and n, m are integers between 1 and 100 and wherein X and Y are covalently bound to P.
b) Contacting the sample of biological specimens with at least one conjugate, thereby labelling the target moiety recognized by the antigen recognizing moiety Y.
c) Detecting the target moiety labelled with the conjugate with the detecting moiety X.
d) Enzymatically degrading spacer P, thereby cleaving the detection moiety X from the conjugate.

With the method of the invention, a fast and reliable method to specifically detect one or more different targets moieties simultaneously or sequentially by signals originating from the detection moiety and subsequent release of the detection moiety after analysis is provided. The "enzymatically quenching" of the detection moieties by the method enables a faster and less invasive protocol for the analysis of biological specimen. Compared to prior art technologies the present method avoids the implementation of reactive oxygen species, high energy or heat which may be harmful for the object of interest and enables the reversible labelling of multiple target moieties simultaneously. Additionally the degradation/disassembly of the conjugate assures less steric hindrance if high numbers of staining (detection) cycles are used.

BRIEF DESCRIPTION OF THE DRAWINGS

Various exemplary details are described with reference to the following figures, wherein.

It should be understood that the drawings are not necessarily to scale, and that like numbers may refer to like features.

DETAILED DESCRIPTION

Detection moiety X and antigen recognizing moiety Y can be bound covalently or quasi-covalently to the enzymatically degradable spacer P. The terms "covalently or quasi-covalently" refers bonds between X and P and Y and P having a dissociation constant of $\leq 10^{-9}$ M.

The term "cleaving the detection moiety X and/or antigen recognizing moiety Y from the conjugate" means that the bond between X and P is abrogated and detection moiety X and/or the antigen recognizing moiety Y may be removed from the target for example by dissociation or washing.

Figure 3:
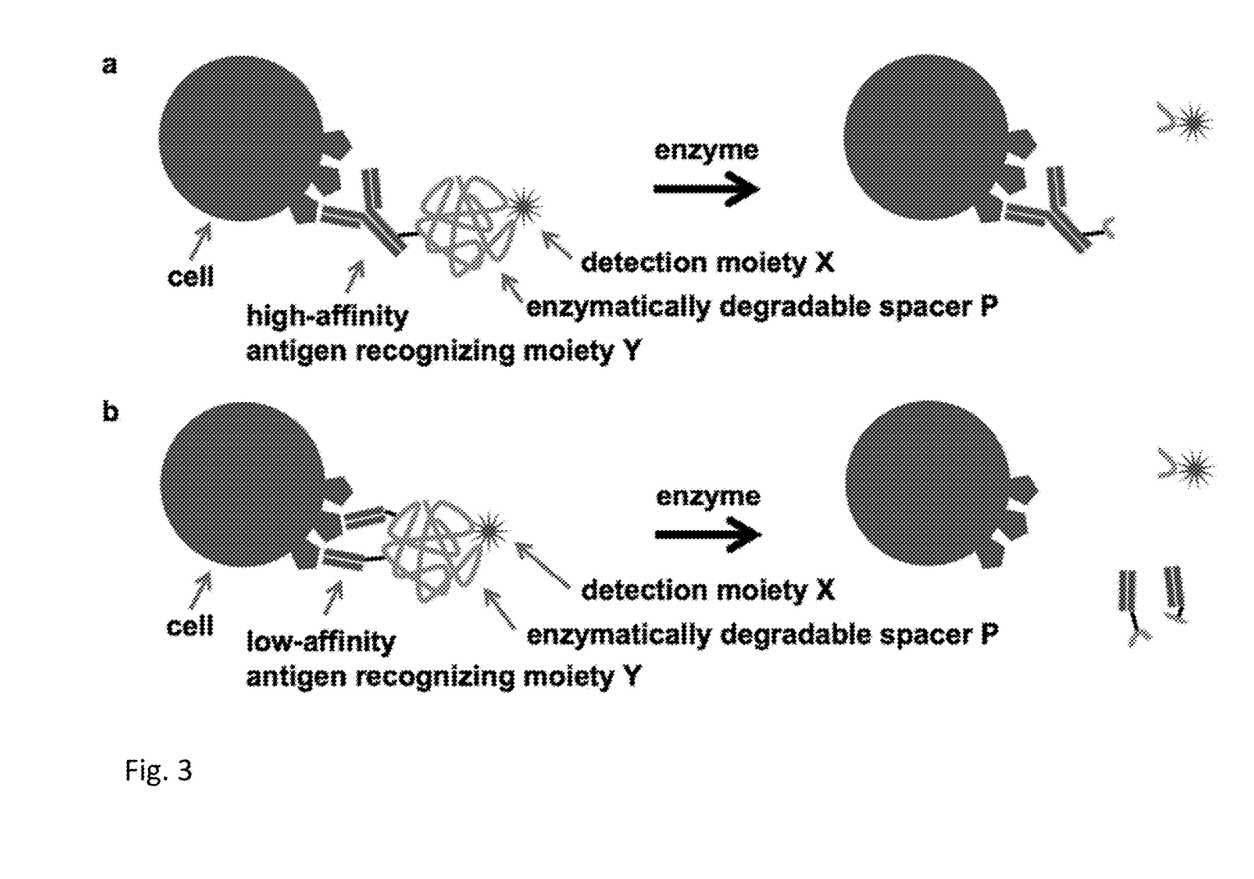
FIG. 3 shows schematically the method of the invention by specific labelling of a target cell as biological specimen with conjugates of high-affinity (a) or low-affinity (b) antigen recognizing moiety Y, enzymatically degradable spacer P and detection moiety X.

FIG. 3 shows schematically the method of the invention by specific labeling of a target cell as biological specimen with conjugates of high-affinity (a) or low-affinity (b) antigen recognizing moiety Y, enzymatically degradable spacer P and detection moiety X. When the spacer is enzymatically degraded, a high-affinity antigen recognizing moiety like, e.g., an antibody, provides a stable bond which results in the removal of the detection moiety X and the spacer P (a). Low-affinity antigen recognizing moieties will be monomerized during the degradation. After dissociation of the low-affinity antigen recognizing moietiy the antigen is removed from the detection moiety X, the spacer P and the antigen recognizing moiety Y (b).

The process of the invention may be performed in one or more sequences of the steps a) to d). After each sequence, the detection moiety and optionally the antigen recognizing moiety is released (removed) from the target moiety. Especially when the biological specimens are living cells which shall be further processed, the method of the invention has the advantage of providing unlabelled cells.

After and/or before each step a)-d), a washing step e) can be performed to remove unwanted material like unbound conjugates or released detection moieties from the sample.

Target Moiety

The target moiety to be detected with the method of the invention can be on any biological specimen, like tissues slices, cell aggregates, suspension cells, or adherent cells. The cells may be living or dead. Preferably, target moieties are antigens expressed intracellular or extracellular on biological specimen like whole animals, organs, tissues slices, cell aggregates, or single cells of invertebrates, (e.g., *Caenorhabditis elegans, Drosophila melanogaster*), vertebrates (e.g., *Danio rerio, Xenopus laevis*) and mammalians (e.g., *Mus musculus, Homo sapiens*).

Detection Moiety

The detection moiety X of the conjugate may be any moiety possessing a property or function which can be used for detection purposes like those selected from the group consisting of chromophore moiety, fluorescent moiety, phosphorescent moiety, luminescent moiety, light absorbing moiety, radioactive moiety, and transition metal isotope mass tag moiety.

Suitable fluorescent moieties are those known from the art of immunofluorescence technologies, e.g., flow cytometry or fluorescence microscopy. In these embodiments of the invention, the target moiety labelled with the conjugate is detected by exciting the detection moiety X and detecting the resulting emission (photoluminescence). In this embodiment, the detection moiety X is preferably a fluorescent moiety.

Useful fluorescent moieties might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyrromethenes, or metallo-organic complexes, such as Ru, Eu, Pt complexes. Besides single molecule entities, clusters of fluorescent proteins or small organic molecule dyes, as well as nanoparticles, such as quantum dots, upconverting nanoparticles, gold nanoparticles, dyed polymer nanoparticles can also be used as fluorescent moieties.

Another group of photoluminescent detection moieties are phosphorescent moieties with time-delayed emission of light after excitation. Phosphorescent moieties include metallo-organic complexes, such as Pd, Pt, Tb, Eu complexes, or nanoparticles with incorporated phosphorescent pigments such as lanthanide doped $SrAl_2O_4$.

In another embodiment of the invention the target labeled with the conjugate is detected without prior excitation by irradiation. In this embodiment the detection moiety can be a radioactive label. They may be in the form of radioisotope labelling by exchanging non-radioactive isotopes for their radioactive counterparts, such as tritium, $^{32}P$, $^{35}S$ or $^{14}C$, or introducing covalently bound labels, such as $^{125}I$, which is bound to tyrosine, $^{18}F$ within fluorodeoxyglucose, or metallo-organic complexes, i.e. $^{99}Tc$-DTPA.

In another embodiment the detection moiety is capable of causing chemiluminescence, i.e. horseradish peroxidase label in the presence of luminol.

In another embodiment of the invention the target labeled with the conjugate is not detected by radiation emission, but by absorption of UV, visible light, or NIR radiation. Suitable light-absorbing detection moieties are light absorbing dyes without fluorescence emission, such as small organic molecule quencher dyes like N-aryl rhodamines, azo dyes, and stilbenes.

In another embodiment, the light-absorbing detection moieties X can be irradiated by pulsed laser light, generating an photoacoustic signal.

In another embodiment of the invention the target labeled with the conjugate is detected by mass spectrometric detection of a transition metal isotope. Transition metal isotope mass tag labels might be introduced as covalently bound metallo-organic complexes or nanoparticle component. Known in the art are isotope tags of lanthanides and adjacent late transition elements.

The detection moiety X can be covalently or non-covalently coupled to the spacer P. Methods for covalently or non-covalently conjugation are known by persons skilled in the art. In case of a covalent bond between the detection moiety X and the spacer P, a direct reaction of an activated group either on the detection moiety or on the spacer P with an functional group on either the spacer P or on the detection moiety X or via an heterobifunctional linker molecule, which is firstly reacted with one and secondly reacted with the other binding partner is possible.

For example, a large number of heterobifunctional compounds are available for linking to entities. Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-y-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, succinimidyl-[(N-maleimidopropionamido) polyethyleneglycol] esters (NHS-PEG-MAL), and succinimidyl 4-[N-maleimidomethyl]cyclohexane-1-carboxylate. A preferred linking group is 3-(2-pyridyldithio)propionic acid N-hydroxysuccinimide ester (SPDP), or 4-(N-maleimidomethyl)cyclohexane-1-carboxylic acid N-hydroxysuccinimide ester (SMCC) with a reactive sulfhydryl group on the detection moiety and a reactive amino group on the spacer P.

A quasi-covalent binding of the detection moiety X to the spacer P can be achieved with binding systems providing a dissociation constant of $\leq 10^{-9}$ M, e.g., Biotin-Avidin binding interaction.

Enzymatically Degradable Spacer P

The enzymatically degradable spacer P can be any molecule which can be cleaved by a specific enzyme, especially a hydrolase. Suitable as enzymatically degradable spacer P are, for example, polysaccharides, proteins, peptides, depsipeptides, polyesters, nucleic acids, and derivatives thereof.

Suitable polysaccharides are, for example, dextrans, pullulans, inulins, amylose, cellulose, hemicelluloses, such as xylan or glucomannan, pectin, chitosan, or chitin, which may be derivatized to provide functional groups for covalent or non-covalent binding of the detection moiety X and the antigen recognizing moiety Y. A variety of such modifications are known in the art, for example, imidazolyl carbamate groups may be introduced by reacting the polysaccharide with N,N'-carbonyl diimidazole. Subsequently amino groups may be introduced by reacting said imidazolyl carbamate groups with hexane diamine Polysaccharides may also be oxidized using periodate to provide aldehyde groups or with N,N'-dicyclohexylcarbodiimide and dimethylsulfoxide to provide ketone groups. Aldehyde or ketone functional groups can be reacted subsequently preferably under conditions of reductive amination either with diamines to provide amino groups or directly with amino substituents on a proteinaceous binding moiety. Carboxymethyl groups may be introduced by treating the polysaccharide with chloroacetic acid. Activating the carboxy groups with methods known in the art which yield activated esters such N-hydroxysuccinimid ester or tetrafluorophenyl ester allows for reaction with amino groups either of a diamine to provide amino groups or directly with an amino group of a proteinaceous binding moiety. It is generally possible to introduce functional group bearing alkyl groups by treating polysaccharides with halogen compounds under alkaline conditions. For example, allyl groups can be introduced by using allyl bromide. Allyl groups can further be used in a thiol-ene reaction with thiol bearing compounds such as cysteamine to introduce amino groups or directly with a proteinaceous binding moiety with thiol groups liberated by reduction of disulfide bonds or introduced by thiolation for instance with 2-iminothiolane.

Proteins, peptides, and depsipeptides used as enzymatically degradable spacer P can be functionalized via side chain functional groups of amino acids to attach detection moiety X and antigen recognizing moiety Y. Side chains functional groups suitable for modification are for instance amino groups provided by lysine or thiol groups provided by cysteine after reduction of disulfide bridges.

Polyesters and polyesteramides used as enzymatically degradable spacer P can either be synthesized with co-monomers, which provide side chain functionality or be subsequently functionalized. In the case of branched polyesters functionalization can be via the carboxyl or hydroxyl end groups. Post polymerization functionalization of the polymer chain can be, for example, via addition to unsaturated bonds, i.e. thiolene reactions or azide-alkine reactions, or via introduction of functional groups by radical reactions.

Nucleic acids used as enzymatically degradable spacer P are preferably synthesized with functional groups at the 3' and 5' termini suitable for attachment of the detection moiety X and antigen recognizing moiety Y. Suitable phosphoramidite building blocks for nucleic acid synthesis providing for instance amino or thiol functionalities are known in the art.

The enzymatically degradable spacer P can be composed of more than one different enzymatically degradable units, which are degradable by the same or different enzyme.

Antigen Recognizing Moiety Y

The term "antigen recognizing moiety Y" refers to any kind of antibody, fragmented antibody or fragmented antibody derivatives, directed against the target moieties expressed on the biological specimens, like antigens expressed intracellular or extracellular on cells. The term relates to fully intact antibodies, fragmented antibody or fragmented antibody derivatives, e.g., Fab, Fab', F(ab')2, sdAb, scFv, di-scFv, nanobodies. Such fragmented antibody derivatives may be synthesized by recombinant procedures including covalent and non-covalent conjugates containing these kind of molecules. Further examples of antigen recognizing moieties are peptide/MHC-complexes targeting TCR molecules, cell adhesion receptor molecules, receptors for costimulatory molecules, artificially engineered binding molecules, e.g., peptides or aptamers which target, e.g., cell surface molecules.

The conjugate used in the method of the invention may comprise up to 100, but preferably 1-20 antigen recognizing moieties Y. The interaction of the antigen recognizing moiety with the target antigen can be of high or low affinity. Binding interactions of a single low-affinity antigen recognizing moiety is too low to provide a stable bond with the antigen. Low-affinity antigen recognizing moieties can be multimerized by conjugation to the enzymatically degradable spacer P to furnish high avidity. When the spacer P is enzymatically cleaved in step d), the low-affinity antigen recognizing moieties will be monomerized which results in a complete removal of the detection moiety X, the spacer P and the antigen recognizing moiety Y (FIG. 3b). High-affinity antigen recognizing moieties provide a stable bond which results in a removal of the detection moiety X and the spacer P during step d).

Preferably, the term "Antigen recognizing moiety Y" refers to an antibody directed against antigen expressed by the biological specimens (target cells) intracellular, like IL2, FoxP3, CD154, or extracellular, like CD3, CD14, CD4, CD8, CD25, CD34, CD56, and CD133.

The antigen recognizing moieties Y, especially antibodies, can be coupled to the spacer P through side chain amino or sufhydryl groups. In some cases the glycosidic side chain of the antibody can be oxidized by periodate resulting in aldehyde functional groups.

The antigen recognizing moiety Y can be covalently or non-covalently coupled to the spacer P. Methods for covalent or non-covalent conjugation are known by persons skilled in the art and the same as mentioned for conjugation of the detection moiety X.

The method of the invention is especially useful for detection and/or isolation of specific cell types from complex mixtures and may comprise more than one sequential or parallel sequences of the steps a)-d). The method may use a variety of combinations of conjugates. For example, a conjugate may comprise antibodies specific for two different epitopes, like two different anti-CD34 antibodies. Different antigens may be addressed with different conjugates comprising different antibodies, for example, anti-CD4 and anti-CD8 for differentiation between two distinct T-cell-populations or anti-CD4 and anti-CD25 for determination of different cell subpopulations like regulatory T-cells.

Enzymes

The choice of enzyme as release agent is determined by the chemical nature of the enzymatically degradable spacer P and can be one or a mixture of different enzymes. Enzymes are preferably hydrolases, but lyases or reductases are also possible. For example, if the spacer P is a polysaccharide, glycosidases (EC 3.2.1) are most suitable as release agents. Preferred are glycosidases that recognize specific glycosidic structures, e.g., dextranase (EC3.2.1.11), which cleaves at the α(1->6) linkage of dextrans, pullulanases, which cleaves either α((1->6) linkages (EC 3.2.1.142) or α((1->6) and α((1->4) linkages (EC 3.2.1.41) of pullulans, neopullulanase (EC 3.2.1.135), and isopullulanase (EC 3.2.1.57), which cleaves α((1->4) linkages in pullulans. α(Amylase (EC 3.2.1.1), and maltogenic amylase (EC 3.2.1.133), which cleaves α(1->4) linkages in amylose, inulinase (EC 3.2.1.7), which cleaves β(2->1) fructosidic linkages in inulin, cellulase (EC 3.2.1.4), which cleaves at the α(1->4) linkage of cellulose, xylanase (EC 3.2.1.8), which cleaves at the α(1->4) linkages of xylan, pectinases such as endo-pectin lyase (EC 4.2.2.10), which cleaves eliminative at the α((1->4) D-galacturonan methyl ester linkages, or polygalacturonase (EC 3.2.1.15), which cleaves at the α(1->4) D-galactosiduronic linkages of pectin, chitosanase (EC 3.2.1.132), which cleaves at the α(1->4) linkages of chitosan and endo-chitinase (EC 3.2.1.14) for cleaving of chitin.

Proteins and peptides may be cleaved by proteinases, which need to be sequence specific to avoid degradation of target structures on cells. Sequence specific proteases are for instance TEV protease (EC 3.4.22.44), which is a cysteine protease cleaving at the sequence ENLYFQ\S, enteropeptidase (EC 3.4.21.9), which is a serine protease cleaving after the sequence DDDDK, factor Xa (EC 3.4.21.6), which is a serine endopeptidase cleaving after the sequences IEGR or IDGR, or HRV3C protease (EC3.4.22.28), which is a cysteine protease cleaving at the sequence LEVLFQ\GP.

Depsipeptides, which are peptides containing ester bonds in the peptide backbone, or polyesters may be cleaved by esterases, such as porcine liver esterase (EC 3.1.1.1) or porcine pancreatic lipase (EC 3.1.1.3). Nucleic acids may be cleaved by endonucleases, which can be sequence specific, such as restriction enzymes (EC 3.1.21.3, EC 3.1.21.4, EC 3.1.21.5), such as EcoRI, HindII or BamHI or more general such as DNAse I (EC 3.1.21.1), which cleaves phosphodiester linkages adjacant to a pyrimidine.

The amount of enzyme added needs to be sufficient to degrade substantially the spacer in the desired period of time. Usually the detection signal is at least about 80%, more usually at least about 95%, preferably at least about 99% reduced. The conditions for release may be empirically optimized in terms of temperature, pH, presence of metal cofactors, reducing agents, etc. The degradation will usually be completed in at least about 15 minutes, more usually at least about 10 minutes, and will usually not be longer than about 30 minutes.

Cell Detection Methods

The method and equipment to detect the target labeled with the conjugate $X_n$—P—$Y_m$ is determined by the detection moiety X.

In one variant of the invention the detection moiety X is a fluorescent moiety. Targets labeled with fluorochrome-conjugate are detected by exciting the fluorescent moiety X and analysing the resulting fluorescence signal. The wavelength of the excitation is usually selected according to the absorption maximum of the fluorescent moiety X and provided by LASER or LED sources as known in the art. If several different detection moieties X are used for multiple colour/parameter detection, care should be taken to select fluorescent moieties having not overlapping absorption spectra, at least not overlapping absorption maxima. In case of a fluorescent moieties as detection moiety the targets may be detected, e.g., under a fluorescence microscope, in a flow cytometer, a spectrofluorometer, or a fluorescence scanner. Light emitted by chemiluminescence can be detected by similar instrumentation omitting the excitation.

In another variant of the invention the detection moiety is a light absorbing moiety, which is detected by the difference between the irradiation light intensity and the transmitted or reflected light intensity. Light absorbing moieties might also be detected by photoacoustic imaging, which uses the absorption of a pulsed laser beam to generate an acoustic like an ultrasonic signal.

Radioactive detection moieties are detected though the radiation emitted by the radioactive isotopes. Suitable instrumentation for detection of radioactive radiation include, for example, scintillation counters. In case of beta emission electron microscopy can also be used for detection.

Transition metal isotope mass tag moieties are detected by mass spectrometric methods such as ICP-MS, which is integrated in mass cytometry instrumentation.

Use of the Method

The method of the invention can be used for various applications in research, diagnostics and cell therapy.

In a first variant of the invention, biological specimens like cells are detected for counting purposes i.e. to establish the amount of cells from a sample having a certain set of antigens recognized by the antigen recognizing moieties of the conjugate.

In a second variant, one or more populations of biological specimens are detected from the sample and separated as target cells. This variant may be used for purification of target cells, for example, in clinical research, diagnostics, and immunotherapy. In this variant, one or more sorting steps may be performed after any of the steps a), b), c,) d) and optionally washing step e).

In another variant, the biological specimens detected by the conjugate in step c) are separated from the sample by optical means, electrostatic forces, piezoelectric forces, mechanical separation or acoustic means. For this purpose, the biological specimens detected by the conjugate in step c) are separated from the sample according to their detection signal to one or more populations simultaneously or subsequently before performing step d) by optical means, electrostatic forces, piezoelectric forces, mechanical separation or acoustic means.

Suitable for such separations are especially flow sorters, e.g., FACS or MEMS-based cell sorter systems, for example as disclosed in EP14187215.0 or EP14187214.3.

In another variant of the invention, the location of the target moieties like antigens on the biological specimens recognized by the antigen recognizing moieties of the conjugate is determined Such techniques are known as "Multi Epitope Ligand Cartography", "Chip-based Cytometry" or "Multioymx" and are described, for example, in EP 0810428, EP1181525, EP 1136822 or EP1224472. In this technology, cells are immobilized and contacted with antibodies coupled to fluorescent moiety. The antibodies are recognized by the respective antigens on the biological specimen (for example on a cell surface) and after removing the unbound marker and exciting the fluorescent moieties, the location of the antigen is detected by the fluorescence emission of the fluorescent moieties. In certain variants, instead of antibodies coupled to fluorescent moieties, antibodies coupled to moieties detectable for MALDI-Imaging or CyTOF can be used. The person skilled in the art is aware how to modify the technique based on fluorescent moiety to work with these detection moieties.

The location of the target moieties is achieved by a digital imaging device with a sufficient resolution and sensitivity for the wavelength of the fluorescence radiation. The digital imaging device may be used with or without optical enlargement for example with a fluorescence microscope. The resulting images are stored on an appropriate storing device like a hard drive, for example in RAW, TIF, JPEG, or HDF5 format.

In order to detect different antigens, different antibody-conjugates having the same or different fluorescent moiety or antigen recognizing moiety Y can be provided. Since the parallel detection of fluorescence emission with different wavelengths is limited, the antibody-fluorochrome-conjugates are utilized sequentially individually or in small groups (2-10) after the other.

In yet another variant of the method according to the invention, the biological specimens—especially suspension cells—of the sample are immobilized by trapping in microcavities or by adherence.

It is furthermore possible to provide next to conjugates with the general formula (I) Xn-P-Ym, with P standing for an enzymatically degradable spacer additional conjugates with the general formula (II) Xn-P'-Ym, with X, Y, n, m having the same meaning as in formula (I) and wherein X and Y are covalently or non-covalently bound to P' but with P' which can be a spacer which is not enzymatically degradable like a PEG spacer. In another variant, at least one non-enzymatically degradable conjugate with the general formula (III) Xn-Ym, wherein X, Y, n, m have the same meaning as in formula (I) can be provided. Non-enzymatically degradable conjugates with the general formula (II) and (III) survive the cleaving steps and can be used for further detection. Non-enzymatically degradable conjugates may be quenched by oxidative or radiation-induced destruction of the fluorescent moiety.

In general, the method of the invention can be performed in several variants. For example, the conjugate not recognized by a target moiety can be removed by washing for example with buffer before the target moiety labelled with the conjugate is detected.

In a variant of the invention, at least two conjugates are provided simultaneously or in subsequent staining sequences, wherein each antigen recognizing moiety Y recognizes different antigens. In an alternative variant, at least two conjugates can be provided to the sample simultaneously or in subsequent staining sequences, wherein each conjugate comprises a different enzymatically degradable spacer P which is cleaved by different enzymes. In both cases, the labelled target moieties can be detected simultaneously or sequentially. Sequential detection may involve simultaneous enzymatically degrading of the spacer molecules P or subsequent enzymatically degrading of the spacer molecules P with optionally intermediate removing (washing) of the non-bonded moieties.

Another variant of the invention comprises the elimination of a fluorescence emission by a combination of enzymatic degradation and oxidative bleaching. The necessary chemicals for bleaching are known from the above-mentioned publications on "Multi Epitope Ligand Cartography", "Chip-based Cytometry" or "Multioymx" technologies.

The method of the invention can be performed in the following embodiments:

Embodiment A of the invention is characterized by contacting the sample of biological specimens in step b) simultaneously with at least a first and a second conjugate having different detection moieties X and/or different enzymatically degradable spacer P and/or different antigen recognizing moieties Y and performing the detection and cleaving of each conjugate in subsequent steps c) and d). The cleaving steps may be performed with the same or a different enzyme.

Embodiment B of the invention is characterized by contacting the sample of biological specimens in step b) simultaneously with at least a first and a second conjugate having different detection moieties X and/or different enzymatically degradable spacer P and/or different antigen recognizing moieties Y and simultaneous performing the detection and cleaving of each conjugate in step c) and d).

Figure 7:
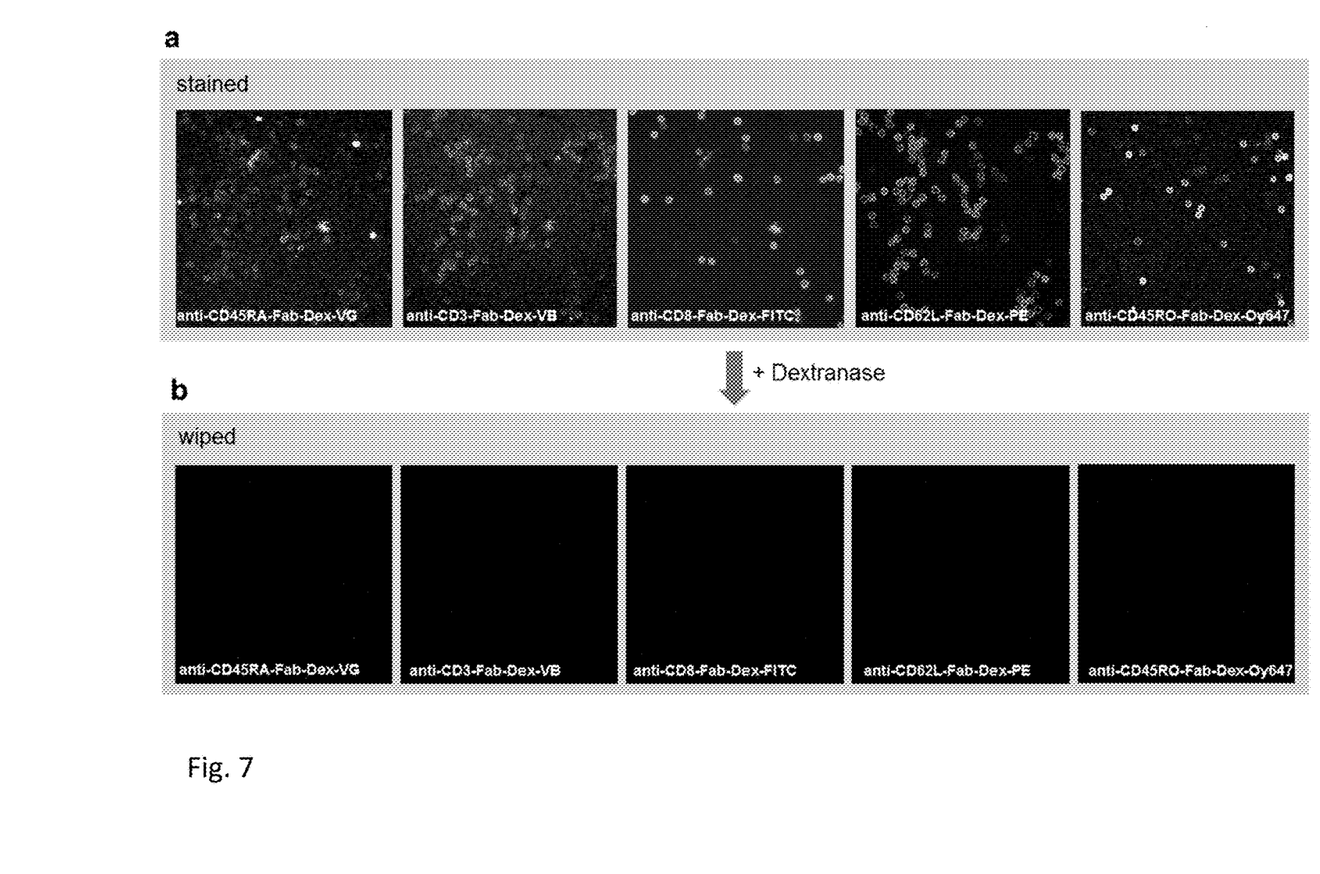
FIG. 7 shows images of simultaneous five parameter labelling conjugates according to the invention having different antigen recognizing moieties and detection moieties. Different cell surface markers can be localized on the cells which enables the determination of different cell populations or subpopulations.

Example 2 (FIGS. 4 and 5) and example 3 (FIG. 7) demonstrate the effectiveness of this embodiment. Here, different PBMC populations are simultaneously labelled with three or five Fab-dextran-fluorochrome-conjugates which enables differentiation of the cells by flow cytometry analysis (FIG. 4a and FIG. 5a) respectively localization of the surface markers on the cells by fluorescence microscopy (FIG. 7a). The fluorescent moieties are simultaneously enzymatically cleaved by dextranase, which is proven by flow cytometry analysis (FIG. 4b and FIG. 5b) respectively fluorescence microscopy (FIG. 7b). This variation provides a fast and specific multiple parameter labelling for the simultaneous detection and/or isolation of different cell populations or cell subpopulations.

Embodiment C of the invention is characterized by contacting the sample of biological specimens with at least a first and a second conjugate having different detection moieties X and/or different enzymatically degradable spacer P and/or different antigen recognizing moieties Y in subsequent sequences comprising steps a) to d).

Figure 6:
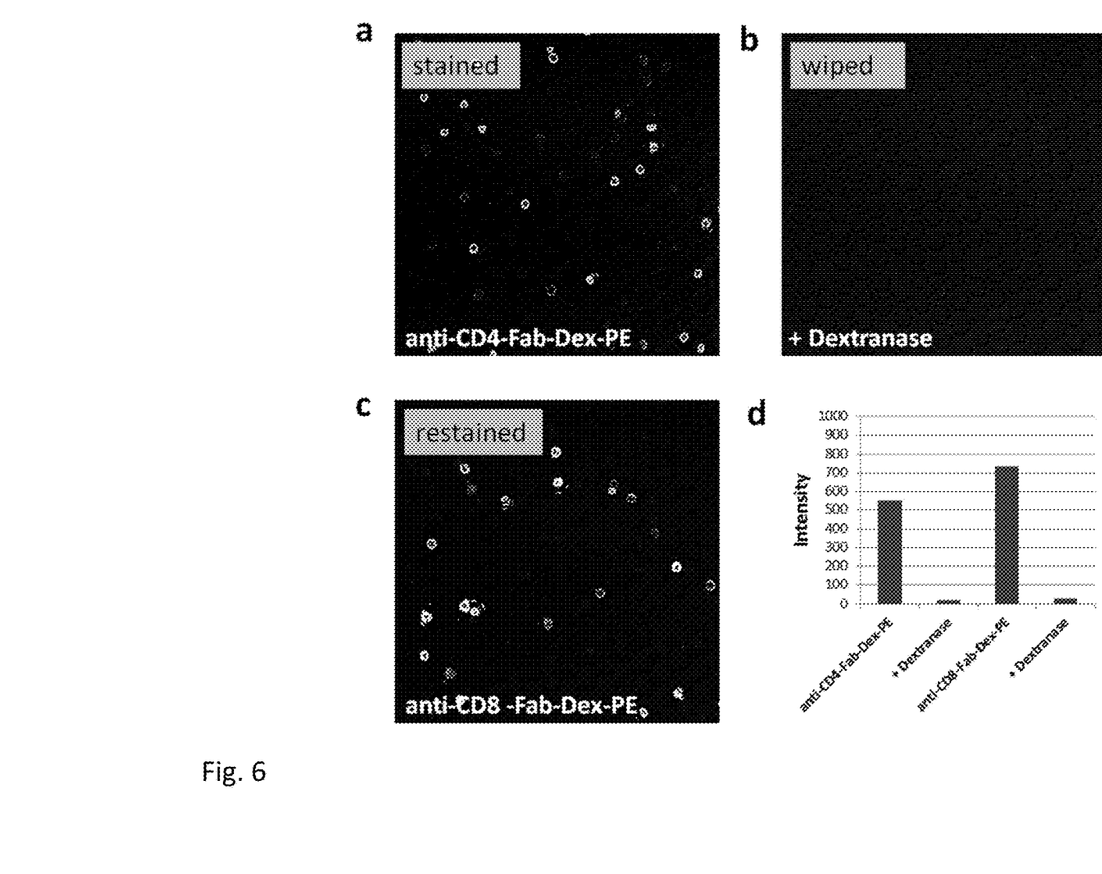
FIG. 6 shows images of a sequential two parameter labelling conjugates according to the invention having different antigen recognizing moieties and detection moieties.

Example 3 (FIG. 6) is performed according to embodiment C. PBMCs are sequentially labelled in subsequent sequences with anti-CD4-Fab-dextran-PE (anti-CD4-Fab-Dex-PE, FIG. 6a) respectively anti-CD8-Fab-dextran-PE (anti-CD8-Fab-Dex-PE, FIG. 6c) which enables localization of the surface markers on the cells by fluorescence microscopy (FIGS. 6a and 6c). In each sequence of this embodiment, the fluorescence signal was eliminated by an enzymatic degradation of the Fab-dextran-fluorochrome-conjugate (FIG. 6b).

This embodiment may optionally comprise a washing step e) to remove cleaved detection moieties X (i.e. after step d)) and/or a washing step e) to remove unbound conjugates after step b).

Embodiment D of the invention is characterized by contacting the sample of biological specimens with at least a first and a second conjugate having different detection moieties X and/or different enzymatically degradable spacer P and/or different antigen recognizing moieties Y in subsequent sequences comprising steps a) to c) and simultaneously performing the cleaving of the conjugates in a single step d)

Embodiment E of the invention is characterized by contacting the sample of biological specimens with at least a first and a second conjugate having different detection moieties X and/or different enzymatically degradable spacer P and/or different antigen recognizing moieties Y in subsequent sequences comprising steps a) to c) and performing the cleaving of each conjugate in subsequent steps d).

Embodiment F of the invention is characterized by contacting the sample of biological specimens with at least a first and a second conjugate having different detection moieties X and/or different enzymatically degradable spacer P and/or different antigen recognizing moieties Y in subsequent sequences comprising steps a) to d) (optionally washing step e)) to remove cleaved detection moieties X) wherein step d) of the first conjugate and step b) of the second conjugate are performed simultaneously.

Compared to embodiment C, a process according to embodiment F provides a reduction of time for multiple cycles of labelling, detection, and enzymatically degradation of spacer P.

EXAMPLES

Example 1

Multiple Parameter Cell Surface Staining with Reversible Indirect PEO-Biotin/Anti-Biotin-system Control: PBMCs in PBS/EDTA/BSA-buffer were stained for 10 min at 4° C. with anti-CD8-APC and anti-CD4-PE. The cells were washed and analysed by flow cytometry.

Complex A-D were prepared by incubating anti-CD8-PEO-Biotin+anti-Biotin-APC (A); anti-CD4-PEO-Biotin+anti-Biotin-PE (B); anti-CD8-PEO-Biotin+anti-Biotin-PE (C); anti-CD4-PEO-Biotin+anti-Biotin-APC (D) 15 h at 4° C.

PBMCs in PBS/EDTA/BSA-buffer were stained for 10 min at 4° C. with complex A (anti-CD8-PEO-Biotin/anti-Biotin-APC) or C (anti-CD8-PEO-Biotin/anti-Biotin-PE). The cells were washed with cold PBS/EDTA/BSA-buffer and stained for 10 min at 4° C. with complex B (anti-CD4-PEO-Biotin/anti-Biotin-PE) or D (anti-CD4-PEO-Biotin/anti-Biotin-APC). The cells were washed with cold PBS/EDTA-BSA-buffer and analysed by flow cytometry. Antibody-PEO-Biotin-conjugates were prepared according to EP2725359 A1.

FIG. 2 shows exemplary dotplots of a typical result of flow cytometry analysis of a multiple parameter labelling with different antibodies in a direct and reversible indirect labelling system. In the control experiment cells were labelled with direct conjugates anti-CD4-PE and anti-CD8-APC, where antibody and fluorescent dye are covalently linked (c). The same antibodies and fluorescent dyes linked via a reversible indirect Biotin/anti-Biotin-binding interaction (visualized in FIG. 1) results in a significant exchange of anti-Biotin-fluorochrome-conjugates which is shown exemplary in FIG. 2a and b. The degree of exchange is dependent on parameters such as the labelling conditions (sequentially or simultaneously labelling of complexes), the concentration of the components of the complex, the selection of anti-Biotin-fluorochrome-conjugate. An example for one of the best cases is shown in a) and worst cases in b). In b), fluorescence signal of CD8+-cells is higher in the APC-channel which was addressed for CD4+-cells by complex D (anti-CD4-PEO-Biotin/anti-Biotin-APC) than in the PE-channel which was originally addressed by labelling with complex C (anti-CD8-PEO-Biotin/anti-Biotin-PE). This exchange of the components of the complexes leads to an incalculable fluorescence signal of target cells in multiple parameter analysis.

Example 2

Reversible Multiple Parameter Cell Surface Staining and Flow Cytometry Analysis with Direct Fab-dextran-fluorochrome-conjugates To prepare antibody- or Fab-dextran-fluorochrome-conjugates with protein-based fluorescent moieties, e.g., PE or APC antibody or Fab was reduced with 10 mM DTT in MES-buffer. After 90 mM incubation time at room temperature, the antibody was purified by size exclusion chromatography utilizing PBS/EDTA-buffer. The protein-based fluorescent moiety was thiolized by incubation with 2-iminothiolane for 60 min at room temperature. The fluorescent moiety was purified by size exclusion chromatography utilizing PBS/EDTA-buffer. Aminodextran was activated by incubation with SMCC for 60 min at room temperature and purified by size exclusion chromatography utilizing PBS/EDTA-buffer. For the conjugation of the antibody- or Fab-dextran-fluorochrome-conjugate activated Fab or antibody and fluorescent moiety were first mixed and then added to the activated dextran. After 60 min incubation time at room temperature, β-mercaptoethanol followed by N-ethylmaleimide were added with a molar excess to block unreacted maleimide- or thiol-functional groups. The antibody- or Fab-dextran-fluorochrome-conjugate was purified by size exclusion chromatography utilizing PBS/EDTA-buffer. The concentrations of antibody or Fab and fluorescent moiety were determined by the absorbance at 280 nm and absorbance at the specific wavelength of the fluorescent dye.

To prepare antibody- or Fab-dextran-fluorochrome-conjugates with small organic molecule dyes, e.g., fluorescein aminodextran was incubated with NHS-activated small molecule dye. After 60 min incubation time at room temperature, the dextran-Fluorochrome-conjugate was purified by size exclusion chromatography utilizing PBS/EDTA-buffer. The dextran-fluorochrome-conjugate was further activated by incubation with SMCC for 60 min at room temperature and purified by size exclusion chromatography utilizing PBS/EDTA-buffer. Antibody or Fab was reduced with 10 mM DTT in MES-buffer. After 90 min incubation time at room temperature, the antibody was purified by size exclusion chromatography utilizing PBS/EDTA-buffer. For the conjugation of the antibody- or Fab-dextran-fluorochrome-conjugate activated Fab or antibody was added to the activated dextran. After 60 min incubation time at room temperature, β-mercaptoethanol followed by N-ethylmaleimide were added with a molar excess to block unreacted maleimide- or thiol-functional groups. The antibody- or Fab-dextran-fluorochrome-conjugate was purified by size exclusion chromatography utilizing PBS/EDTA-buffer. The concentrations of antibody or Fab and fluorescent moiety were determined by the absorbance at 280 nm and absorbance at the specific wavelength of the fluorescent dye.

Three Parameter Labelling

PBMCs in PBS/EDTA/BSA-buffer were stained for 10 mM at 4° C. with anti-CD8-Fab-dextran-Fluorescein, anti-CD4-Fab-dextran-APC, and anti-CD3-Fab-dextran-PE. The cells were washed with cold PBS/EDTA-BSA-buffer and analysed by flow cytometry. For reversibility of the fluorescent labelling cells were incubated with or w/o dextranase for 10 min at 21° C., washed with PBS/EDTA-BSA-buffer and analysed by flow cytometry.

Five Parameter Labelling

PBMCs in PBS/EDTA/BSA-buffer were stained for 10 mM at 4° C. with anti-CD3-Fab-dextran-VioBlue®, anti-CD8-Fab-dextran-Fluorescein, anti-CD45RA-Fab-dextran-VioGreen™, anti-CD45RO-Fab-dextran-Oyster®-647, and anti-CD62L-Fab-dextran-PE. The cells were washed with cold PBS/EDTA-BSA-buffer and analysed by flow cytometry. For reversibility of the fluorescent labelling cells were incubated with or w/o dextranase for 10 min at 21° C., washed with PBS/EDTA-BSA-buffer and analysed by flow cytometry.

Figure 4:
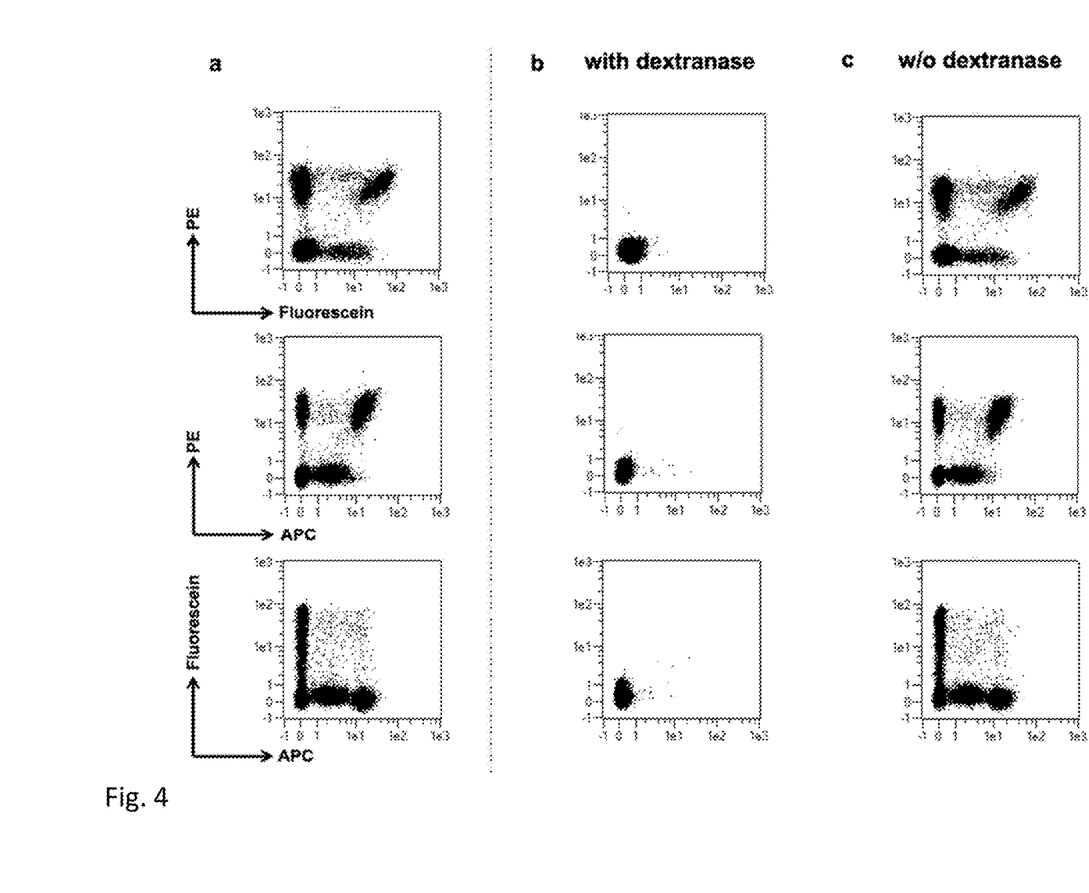
FIG. 4 and FIG. 5 show exemplary dotplots of the result of flow cytometry analysis of a three and five parameter labelling with conjugates according to the invention having different antigen recognizing moieties and detection moieties.
Figure 5:
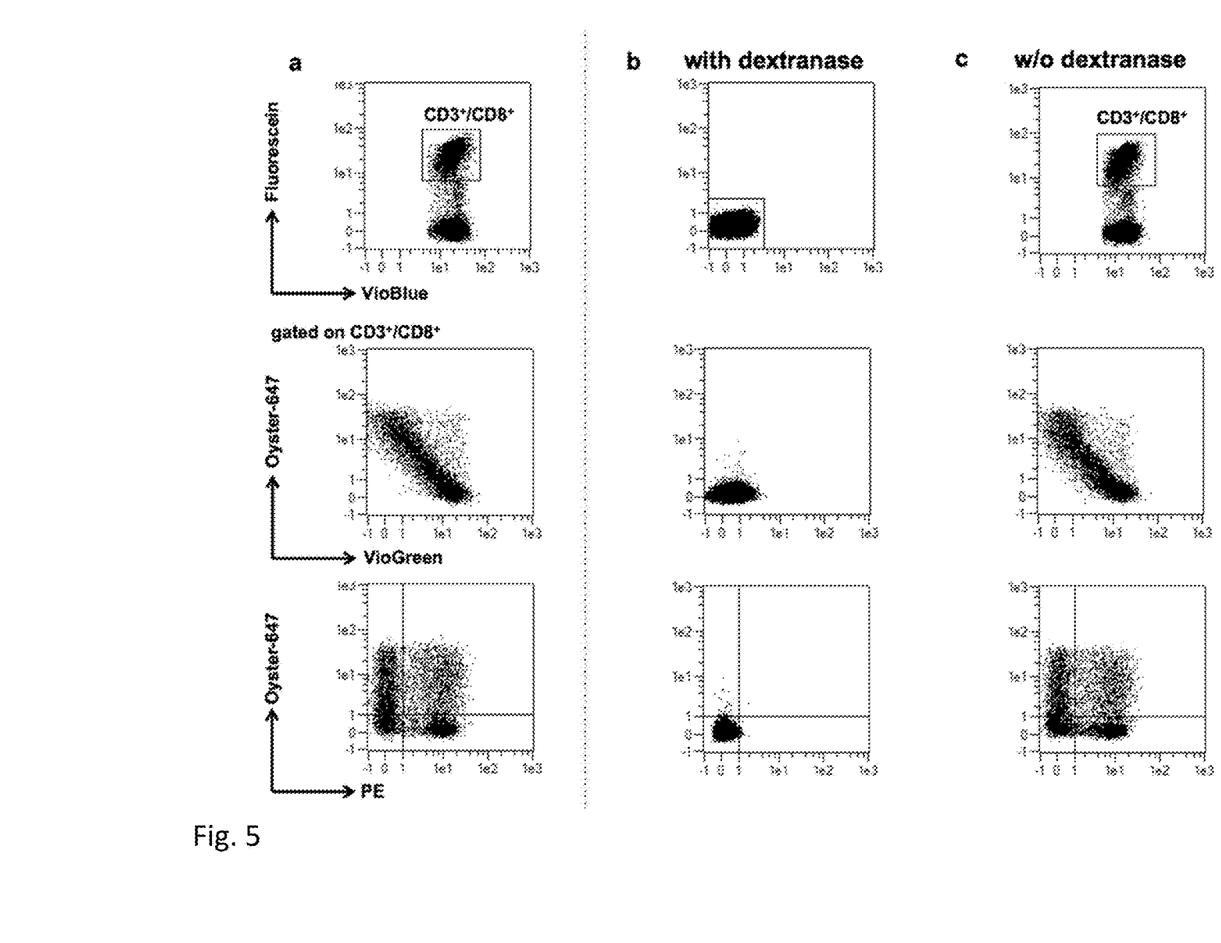

FIGS. 4 and 5 show exemplary dotplots of the result of flow cytometry analysis of a three and five parameter labelling with different Fab-dextran-fluorochrome-conjugates which enabled the determination of different cell populations and cell subpopulations.

For the example with three parameters PBMCs were specifically and simultaneously labelled with anti-CD8-Fab-dextran-Fluorescein (Fluorescein), anti-CD4-Fab-dextran-APC (APC), and anti-CD3-Fab-dextran-PE (PE) (FIG. 4a). Different cell subpopulations were discriminated by exemplary five parameter labelling of PBMCs with anti-CD3-Fab-dextran-VioBlue® (VioBlue), anti-CD8-Fab-dextran-Fluorescein (Fluorescein), anti-CD45RA-Fab-dextran-VioGreen™ (VioGreen), anti-CD45RO-Fab-dextran-Oyster®-647 (Oyster-647), and anti-CD62L-Fab-dextran-PE (PE) (FIG. 5a).

After the addition of dextran-degrading enzyme dextranase remaining fluorescence intensity of the different labelled cell populations was in the range of the detection limit (FIGS. 4b and 5b). W/o Dextranase fluorescence intensity of the cell populations was not affected (FIGS. 4c and 5c).

Example 3

Reversible Sequential and Multiple Parameter Cell Surface Staining and Fluorescence Microscope Analysis with Direct Fab-dextran-fluorochrome-conjugates Fab-dextran-conjugates were prepared accordingly to example 2.

Sequential Two Parameter Labelling

PBMCs in PBS/EDTA/BSA-buffer were captured in a CytoCapture dish by sedimentation. First, the cells were stained for 10 min at 21° C. with anti-CD4-Fab-dextran-PE, washed with PBS/EDTE/BSA-buffer and images taken with a fluorescence microscope. For reversibility of the fluorescent labelling cells were incubated with dextranase for 10 min at 21° C. and again washed with PBS/EDTA/BSA-buffer and images taken with a fluorescence microscope. Second, the sample was restained with anti-CD8-Fab-dextran-PE and afterwards the fluorescent label was released using the same procedure as described for anti-CD4-Fab-dextran-PE. For the analysis cell specific fluorescence intensity values were extracted from the taken images via an object-identification algorithm.

Five Parameter Labelling

PBMCs in PBS/EDTA/BSA-buffer were stained with anti-CD3-Fab-dextran-VioBlue®, anti-CD8-Fab-dextran-Fluorescein, anti-CD45RA-Fab-dextran-VioGreen™, anti-CD45RO-Fab-dextran-Oyster®-647, and anti-CD62L-Fab-dextran-PE. The cells were washed with PBS/EDTA-BSA-buffer and analysed by fluorescence microscopy. For reversibility of the fluorescent labelling cells were incubated with dextranase for 10 min at 21° C., again washed with PBS/EDTA/BSA-buffer and analysed by fluorescence microscopy.

FIGS. 6 and 7 show exemplary images taken with a fluorescence microscope of a sequential two and a simultaneous five parameter labelling with different Fab-dextran-fluorochrome-conjugates which enabled the localization of different cell surface markers on the cells and the determination of different cell populations and cell subpopulations.

For the example of a sequential two parameter labelling PBMCs were labelled with anti-CD4-Fab-dextran-PE (anti-CD4-Fab-Dex-PE, FIG. 6a) respectively anti-CD8-Fab-dextran-PE (anti-CD8-Fab-Dex-PE, FIG. 6c) and analysed by fluorescence microscopy. Between the two labelling and detection steps the fluorescence signal was eliminated by an enzymatic degradation of the Fab-dextran-fluorochrome-conjugate (FIG. 6b). FIG. 6d shows the statistical analysis of all images.

For the five parameter labelling PBMCs were stained simultaneously with anti-CD3-Fab-dextran-VioBlue® (anti-CD3-Fab-Dex-VB), anti-CD8-Fab-dextran-Fluorescein (anti-CD8-Fab-Dex-FITC), anti-CD45RA-Fab-dextran-VioGreen™ (anti-CD45RA-Fab-Dex-VG), anti-CD45RO-Fab-dextran-Oyster®-647 (anti-CD45RO-Fab-Dex-Oy647), and anti-CD62L-Fab-dextran-PE (anti-CD62L-Fab-Dex-PE) (FIG. 7a).

After the addition of dextran-degrading enzyme dextranase remaining fluorescence intensity of the different labelled cell populations was in the range of the background signal (FIG. 7b) enabling further sequential multiple parameter labelling and detection cycles.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Furthermore, details related to the specific methods, dimensions, materials uses, shapes, fabrication techniques, etc. are intended to be illustrative only, and the invention is not limited to such embodiments. Descriptors such as top, bottom, left, right, back front, etc. are arbitrary, as it should be understood that the systems and methods may be performed in any orientation. Accordingly, the exemplary implementations set forth above, are intended to be illustrative, not limiting.

What is claimed is:

1. A method for detecting a target moiety in a sample of biological specimens by:
    a) providing at least one conjugate with the general formula (I) $X_n$—P—$Y_m$, wherein X is a detection moiety, P is an enzymatically degradable spacer, Y is an antigen recognizing moiety and n, m are integers between 1 and 100 and wherein X and Y are covalently bound to P;
    b) contacting the sample of the biological specimens with the at least one conjugate, thereby labelling the target moiety recognized by the antigen recognizing moiety Y;
    c) detecting the target moiety labelled with the conjugate; and
    d) enzymatically degrading the spacer P, thereby cleaving the detection moiety X from the conjugate,
        wherein the detection moiety X is a fluorescent moiety, the enzymatically degradable spacer P is dextran, and the antigen recognizing moiety Y is Fab, and
        wherein by enzymatically degrading the spacer P, the antigen recognizing moiety Y is also cleaved from the target moiety.

2. The method according to claim 1, wherein the biological specimens are separated from the sample by at least one of electrostatic forces, piezoelectric forces and mechanical separation.

* * * * *